US012678057B2

(12) United States Patent
Lovoi

(10) Patent No.: US 12,678,057 B2
(45) Date of Patent: Jul. 14, 2026

(54) METHOD OF DETERMINING RECOVERY FROM CONCUSSION

(71) Applicant: The Regents of the University of California, Oakland, CA (US)

(72) Inventor: Paul A. Lovoi, Los Altos, CA (US)

(73) Assignee: The Regents of the University of California, Oakland, CA (US)

( * ) Notice: Subject to any disclaimer, the term of this patent is extended or adjusted under 35 U.S.C. 154(b) by 267 days.

(21) Appl. No.: 18/217,973

(22) Filed: Jul. 3, 2023

(65) Prior Publication Data

US 2026/0182844 A1 Jul. 2, 2026

(51) Int. Cl.
*A61B 5/0205* (2006.01)
*A61B 5/00* (2006.01)
*A61B 5/11* (2006.01)
*A61B 5/347* (2021.01)

(52) U.S. Cl.
CPC .......... *A61B 5/0205* (2013.01); *A61B 5/1117* (2013.01); *A61B 5/347* (2021.01); *A61B 5/4064* (2013.01); *A61B 5/6803* (2013.01); *A61B 5/7246* (2013.01); *A61B 5/7257* (2013.01); *A61B 5/7275* (2013.01); *A61B 5/7282* (2013.01); *A61B 5/002* (2013.01); *A61B 2505/01* (2013.01); *A61B 2560/0406* (2013.01); *A61B 2560/045* (2013.01); *A61B 2560/0462* (2013.01); *A61B 2562/0219* (2013.01); *A61B 2562/16* (2013.01)

(58) Field of Classification Search
CPC ..... A61B 5/0205; A61B 5/347; A61B 5/1117;
A61B 5/4064; A61B 5/6803; A61B 5/7246; A61B 5/7257; A61B 5/7275; A61B 5/7282; A61B 5/002; A61B 2505/01; A61B 2560/0406; A61B 2560/045; A61B 2560/0462; A61B 2562/0219; A61B 2562/16
See application file for complete search history.

(56) References Cited

U.S. PATENT DOCUMENTS

| | | |
|---|---|---|
| 8,905,932 B2 | 12/2014 | Lovoi et al. |
| 10,092,195 B2 | 10/2018 | Lovoi et al. |
| 10,307,065 B1 | 6/2019 | Lovoi et al. |
| 10,765,332 B2 | 9/2020 | Harrer et al. |
| 2015/0100141 A1 | 4/2015 | Hughes |
| 2016/0296153 A1 | 10/2016 | Lovoi et al. |
| 2017/0020435 A1 | 1/2017 | Lovoi et al. |
| 2019/0183402 A1 | 6/2019 | Lovoi et al. |
| 2022/0125323 A1 | 4/2022 | Smith et al. |
| 2023/0148942 A1 | 5/2023 | Lovoi et al. |

*Primary Examiner* — Michael T Rozanski
(74) *Attorney, Agent, or Firm* — Thomas M. Freiburger

(57) ABSTRACT

A system and method for detecting or verifying recovery from concussion includes a headset or head-attachable device placed against the head of a patient who has exhibited concussion. In the device is an accelerometer for detecting and measuring natural motions of the head due to blood flow in the brain. After a prescribed number of days post-concussion, when the patient returns to physical activity, the accelerometer data from natural motions are analyzed to determine whether concussion persists. Preferably a gross movement accelerometer is also included in the head-attachable device, to record gross movements of the head, so as to correlate any increase in concussion-indicating data with the return to physical activity.

11 Claims, 12 Drawing Sheets

A

METHOD OF DETERMINING RECOVERY FROM CONCUSSION

BACKGROUND OF THE INVENTION

The invention concerns a method of determining when a subject has suffered a concussive injury and when that subject has recovered from that injury and can safely return to activity. This is assessed using a headset system, the HeadPulse signal, and one or more algorithms. The Head- HeadPulse derives its signal from brain motion and is not subjective, it does not require the subject to cooperate and detection of a concussive injury and recovery from a concussive injury can be carried out on sleeping, unconscious or awake subjects. The non-invasive headset can be placed for a single recording, multiple recordings or worn continuously.

Another aspect of the invention is to provide a monitor of head motion to provide input to the algorithm that determines the subject has recovered from a concussive injury.

Another aspect of the invention is to assure integrity of remote monitoring of concussion recovery.

The terms "concussion" and "mild Traumatic Brain Injury (mTBI)" are used interchangeability in this document. Concussion is defined clinically and is diagnosed by sports medicine trained professionals including emergency physicians, team physicians, coaches, team trainers, physical therapists and others. The term "concussive injury" refers to pathological changes in the brain following a concussion. "Subconcussive Injury" is brain injury sustained due to external forces applied to the brain that do not lead to symptoms of concussion. The unit mq herein stands for mili-g or 0.001 g where g is the acceleration of gravity, 1 q=9.8 m/s².

Traumatic brain injury (TBI) causes significant morbidity and mortality with an annual global incidence exceeding 60 million. One third of injuries are sports related with predilection for young adults. The vast majority of TBI is technically classified as 'mild' using current diagnostic criteria. Concussion is a subset of TBI and symptoms include headache, vestibular impairment, visual changes, cognitive symptoms, mood changes, and sleep disturbance. A second concussion during recovery can be neurologically deleterious and in rare cases fatal ('second impact syndrome'). Repetitive concussive or asymptomatic sub-concussive events are also associated with delayed onset neurorobehavioral impairment and subsequent neuropathological findings of chronic traumatic encephalopathy (CTE) and other neurodegenerative conditions. Risk factors for repetitive head injury and CTE are well described in the literature and include collision sports. To mitigate these risks, most organized sports teams utilize concussion protocols which prohibit return to play before recovery which is also clinically determined. Objective identification of concussive injury, asymptomatic sub-concussive injury, and definitive recovery is critical to mitigate both short and long-term impairment and remains an unmet need.

There exists a digital biomarker derived from cranial accelerometry (CA) which draws on principles of ballistocardiography first recognized in the 19th century. Ballistocardiography measures whole body forces produced by cardiac contraction. Similarly, the motion of the brain due to the cardiac cycle and its induced inflow and outflow of blood in the brain can be measured on the scalp using sensitive accelerometers or other sensor. Herein this is called the 'HeadPulse' and it has previously been shown that frequency domain analysis of the HeadPulse supports a diagnosis of concussive injury and recovery from concussive injury. HeadPulse abnormalities, when processed through the appropriate algorithm, can provide diagnosis—moderate to severe TBI, large vessel occlusion (LVO) stroke, intracranial hemorrhage (ICH), seizure, migraine, cerebral vasospasm, and onset of edema following a cardiac arrest, among other neurological conditions.

Analysis of the HeadPulse signal can indicate when a person has suffered a concussive injury. By processing the HeadPulse signal through a concussion algorithm, various "biometric parameters" are generated that correlate with the diagnosis of recent concussion. We use the term "biometric concussion" to indicate that HeadPulse recordings from an individual significantly exceed values derived from normal, non-concussed individuals and "biometric onset" to indicate the time at which the first recording met the biometric concussion definition. This biometric concussion signal appears after a clinically determined concussion and returns to normal when sufficient time has elapsed and the subject has healed. The time to return to normal varies by how severe the concussion was and how an individual heals.

The Zurich Protocol was developed to help determine when a concussed subject can return to activity. This protocol uses a symptom survey of 22 physiological indicators (Sport Concussion Assessment Tool 2 or SCAT2) such as trouble sleeping, headaches, balance or trouble focusing on tasks, to determine if a subject has suffered a concussion. When the symptom survey returns to a normal (or baseline) score the subject is allowed to start limited exercise. If the symptom survey score increases again, subjects are told to rest again without exercise. When the subject's symptom survey score again returns to baseline, exercise is resumed. When exercise does not result in the symptom survey score increasing, additional, more rigorous exercise is permitted. This is continued until strenuous exercise does not increase the symptom survey score.

The Zurich Protocol approach assumes that the brain is healed when no symptoms occur with exercise. The Zurich Protocol incorrectly assumes that exercise that does not trigger symptoms is not harmful. In addition, the Zurich Protocol requires self-reporting by the subject and is susceptible to gaming of the protocol by subjects that want to return to activity even though they do have symptoms but do not report them. Likewise, subjects may feign symptoms of a concussion to be allowed to not participate in an activity.

This invention avoids the potential of subjects incorrectly self-reporting symptoms and provides a method to determine when it is safe to return to activity after a concussive injury. This invention may also provide a method to determine if a subject has not received a concussive injury.

SUMMARY OF THE INVENTION

The disclosed method of the invention non-invasively measures a physiological parameter, the HeadPulse, that when processed through the concussion algorithm can detect when a subject has received a concussive injury and when the subject has recovered from that injury. The HeadPulse is a physiological measure of concussion that does not require any participation from the subject. A subject that is awake, sleeping, or unconscious can have a concussion diagnosed and can be monitored for recovery which is not possible with other scales or methods that rely on subject participation.

A further disclosed method of the invention uses a gross motion detector in contact with the head to continuously monitor how much force has been delivered to the subject's brain during normal activity. The motion detection data are processed by the concussion recovery algorithm to determine when it is safe to return to activity.

Analysis of HeadPulse biometric parameters indicates a concussion if any of the calculated parameters exceeds its concussion criteria threshold. The HeadPulse concussion biometric indicates recovery from concussive injury in two stages. In stage one, recovery is indicated when any concussion biometric parameter falls below the concussion criteria threshold and continue to decline over time. In stage two, recovery is further indicated when the concussion biometric parameters do not correlate with external forces applied to the head. If motion to the brain, i.e. physical activity, as measured directly on the head, raises the concussion biometric parameters then recovery from concussion is not confirmed even if stage one recovery has been met.

The concussion biometric parameters can be used as a binary test as described above and they can further be used to measure the increase in concussion biometric and recovery from concussion when this biometric falls within normal values. Even when the concussion biometric parameters are below the concussion criteria threshold they continue to decline until they reach a stable baseline. Normal subjects and subjects that have recovered from a concussive injury, have baselines that are below the concussion biometric threshold but vary between individuals. During concussive injury recovery the concussion biometric parameters return smoothly to baseline. When the concussion biometric parameters remain stable over time, the subject has recovered from their injury and can return to strenuous exercise.

To determine the diagnostic sensitivity of the device, a clinical trial can be carried out.

A group of subjects who are free of concussion diagnosis (control subjects) for a defined duration (example 1 year) have a HeadPulse recording and subsequent algorithm analysis. The concussion biometric parameters are calculated for this cohort and averages of these parameters and variance (standard deviation) are derived. Control subjects whose HeadPulse exceeds the concussion biometric parameters by a predefined statistic, for example 2 standard deviations above the mean of the controls, but may be between 1 to 4 standard deviations, are considered false positives, while those falling below this threshold are considered true negatives. It is expected that the false positive rate will be predictable from the definition of the threshold. For example, assuming a normal distribution of values, using a 2 standard deviation threshold, an estimated 2.5% false positive rate is expected and higher or lower false positive rate will apply for thresholds between 1 to 4 standard deviations.

A group of clinically diagnosed concussion subjects have periodic HeadPulse recordings following the concussive event for a prescribed duration, for example, 1 month, but this may be two weeks or up to 6 months. Subjects whose HeadPulse exceeds the concussion biometric parameters by a predefined statistic, for example 2 standard deviations above the mean of the controls, will be registered as concussion. Such subjects will be true positives. For subjects who do not exceed this threshold for a defined period of observation for example, 2 weeks, but this may be between 1 week to 6 months, are considered false negatives.

To determine if a HeadPulse concussion biometric is, in fact, a useful measure of concussion recovery the following clinical trial can be carried out:

A normal subject without concussion is measured when exercising:

If the HeadPulse concussion biometric does not indicate a concussion, using a control population as described above, then this is scored as a true negative.

If the HeadPulse concussion biometric does indicate a concussion, then this is scored as a false positive.

A subject who has suffered a concussion is measured when exercising:

If the HeadPulse concussion biometric does indicate a concussion, then this is scored as a true positive.

If the HeadPulse concussion signature does not indicate a concussion, then this is scored as a false negative.

In the protocol above the determination of when a subject is concussed is based on clinical assessment by a healthcare professional.

An additional problem with the Zurich Protocol is the lack of objective measure of exercise and its influence on the brain. Exercise such as jumping jacks or jogging may be done with varying degrees of rigor, thus making difficult the determination of whether the brain has been shaken significantly to elicit reoccurring symptoms of concussion.

The invention applies a direct method of detecting concussion and a much more sensitive and objective measure of recovery from concussion. A device that includes a low-level accelerometer plus a high-level accelerometer in a single unit, or separate low-level and high-level accelerometers both attached to the head of a subject, can record the amount of gross motion the brain receives from activity, and when the subject is resting, measure the HeadPulse and calculate the concussion signature score. A correlation between the activity and the concussion biometric parameters can be used to determine if a subject has returned to normal and may return to activity. Normal would be when strenuous activity does not trigger an increase in the HeadPulse concussion biometric parameter.

If the accelerometer has sufficient dynamic range, both the low level (~10 mg-40 mg) and the high level (0.5 g-100 g), the accelerometers can be one device. A 24 bit ADC has 23 bits of resolution for a single sided (+100 g) acceleration and a least significant bit (LSB) of 12 μg. Systems with these parameters are readily available.

The dual accelerometer system, either integrated together or combined singly, can be made extremely small and placed in glasses, ear canal, placed in a headset or attached to the head with adhesive. The device can be powered by a primary or secondary battery, solar cell or other power sources. The device can be designed to be off most of the time, to conserve power, and can be powered on at a predetermined interval or by detecting motion. An Application-Specific Integrated Circuit (ASIC) can be designed and manufactured to reduce the cost and size. Advanced power management can be used to maximize the wear time before recharging.

The time course of paired exercise and HeadPulse concussion biometric parameters provide the diagnosis as described above. If the concussed subject is again normal, the HeadPulse concussion biometric parameters will not increase with exercise. The subject can safely return to strenuous exercise, contact sports or military duty.

In a further aspect, the invention helps ensure that self-administered recording of cranial accelerations and activity monitoring is being recorded from the identified subject that has suffered a concussion.

In most instances the concussed subject desires to faithfully monitor recovery and the subject is aware that resuming strenuous activity before the brain has fully healed may have serious sequela. In other instances, there is a strong desire or financial incentive to return to activity despite still having elevated symptoms survey scores or elevated concussion biometric parameters from the HeadPulse system.

There is also a strong desire to return to activity when the symptoms survey score has returned to normal and the cranial acceleration concussion biometric parameters have returned to baseline, but that could rise when activity is resumed. Either a rise in the symptoms survey score or in the concussion biometric parameters would restrict the subject from returning to activity, especially military deployment or contact sports.

HeadPulse recordings taken by a medical professional ensure that the recordings are of the person recovering from a concussion. It is not practical, however, to have a patient always in the presence of a medical professional for repeated recordings to determine the recovery from concussion, which may take several weeks or more.

The invention ensures that the time course of cranial accelerometry data, HeadPulse concussion biometric, are all recorded by the concussed subject and not a stand-in.

The HeadPulse concussion signature does not require subject baseline data and is only elevated when a subject has a concussion. The HeadPulse is recorded by using an accelerometer or other sensor in contact with the subject's head, preferably in the temple region. A smart phone may be used to control the headset or the headset may be self-contained with all concussion biometric parameters being calculated within the headset.

Some subjects will go to great lengths to make recordings that do not indicate concussion by applying the headset to a non-concussed subject thus indicating to the medical professional or other gate keeper that they are fit to continue strenuous exercise, contact sports or military deployment. In other cases a subject may wish to be diagnosed with a concussion when they in fact to not have one.

The invention has several methods to prevent either of these incorrect diagnoses from occurring.

A medical professional will initially enroll the concussed subject in person and take the first recording. When a smart phone is part of the headset system, facial recognition can be deployed to record the subject's face. When additional HeadPulse recordings are required over the recovery period the subject will have to log onto the system using their face for ID. To further ensure that the concussed subject is making the recording, the ECG R peak signal can be correlated with the photoplethysmography signal derived from the well-established skin blush due to the blood surge into the brain and face as detected by the smart phone camera. The HeadPulse app can utilize the R peak timing as transmitted by the headset to the HeadPulse app. This timing can be transmitted wirelessly or the camera can detect a light flash on the headset correlated with the R peak of the ECG. The correlation of the photoplethysmography signal and the R peak of the ECG combined with facial recognition ensure that the recording is being made on the concussed subject.

Another method of this invention to ensure the integrity of the HeadPulse recording is to use the average single heartbeat time domain HeadPulse recording. The HeadPulse signal has been shown to be unique for each subject. This average signal is stable over weeks, months and years and therefore can be used to verify that the signal being recorded is from the same subject as initially enrolled in the concussion recovery protocol.

The device will be used to assess patients referred to medical professionals following the clinical diagnosis of concussion. These clinical evaluations are often 7-10 days following the traumatic brain injury (TBI) and the patient may have a range of symptoms ranging from none to marked. The evaluating medical professional applies the device to the patient's head and the device results in concussion present or concussion absent by calculating the concussion biometric and comparing this result to control data. The test may be repeated at the point of care if desired. This result aids in the discrimination of post-traumatic migraine from concussion. The symptoms of migraine and concussion overlap (nausea, photophobia, dizziness, vomiting, headache) so it is often difficult to determine in which category the patient falls. Subjects who are migraine prone (either have had migraine in the past or have features of migraine without headache) are particularly sensitive to brain trauma in that migraine symptoms can be greatly exacerbated by even minor TBI. A clinician faced with such a patient needs to understand if the patient is having a migraine, a concussion, or a combination of both. The device result helps the clinician decide if migraine treatment, or concussion specific treatment is the best for the patient. For subjects with a clear concussion event with a normal reading, or reading showing current concussion, the device can be prescribed for ambulatory recordings to test if the subject is still sensitive to physical activity and intervene if they are by restricting activity until the device shows recovery. For subjects that do not show concussion with the device, medications and other therapy directed at migraine treatments can be implemented with liberation of physical activity. Migraine subjects can also be monitored on an ambulatory basis to look for concussion recurrence.

The device will be used to screen battle readiness of military participants. Battle readiness covers several domains, including a history of recent head trauma. For military combatants returning to tour of duty, screening with the device aids in the battle readiness decision.

The device will be used to identify the etiology of altered mental status in patients who cannot provide a history of their illness and no bystanders exist to describe the events leading up to the altered mental status. Specifically, across the world bystanders encounter individuals who are poorly responsive to voice or are comatose and call advanced emergency services for evaluation. Pre-hospital providers arrive quickly to assess the patient and focus on their level of consciousness and vital signs (blood pressure, oxygen saturation), spontaneous respiration. The priority is to medically support the patient until arrival to advanced care in a hospital. Once in the hospital emergency services consider many potential etiologies ranging from trauma, stroke, seizure, drug toxicity, shock, and metabolic processes. The device has already been proven to detect large vessel stroke and intracerebral hemorrhage large enough to diminish consciousness; application of the device to facilitate stroke triage is the foundation for copending application Ser. No. 17/423,281. Shock is excluded if the patient has a normal blood pressure. Drug toxicity is revealed with urine toxicology testing, and most metabolic processes are revealed with simple basic metabolic profile serum tests. Head trauma may not be apparent in CT scans of the brain (which are usually obtained on all cases) may not show changes despite the person having a significant traumatic brain injury. Use of the device will reveal the etiology of altered mental status as TBI while additional testing just listed can inform if multiple etiologies coexist. For instance, alcohol intoxication with traumatic brain injury commonly coexists on patients brought to the emergency room. Knowing that TBI is the cause or contributes to the cause of altered mental status aids in the clinical management of the patient so recovery can be maximized. The device aids in the diagnosis of TBI in resource limited environments where CT scanning is not readily available and because of the devices portable nature can be used in the prehospital setting for aiding in triage decisions.

DESCRIPTION OF PREFERRED EMBODIMENTS

Figure 1:
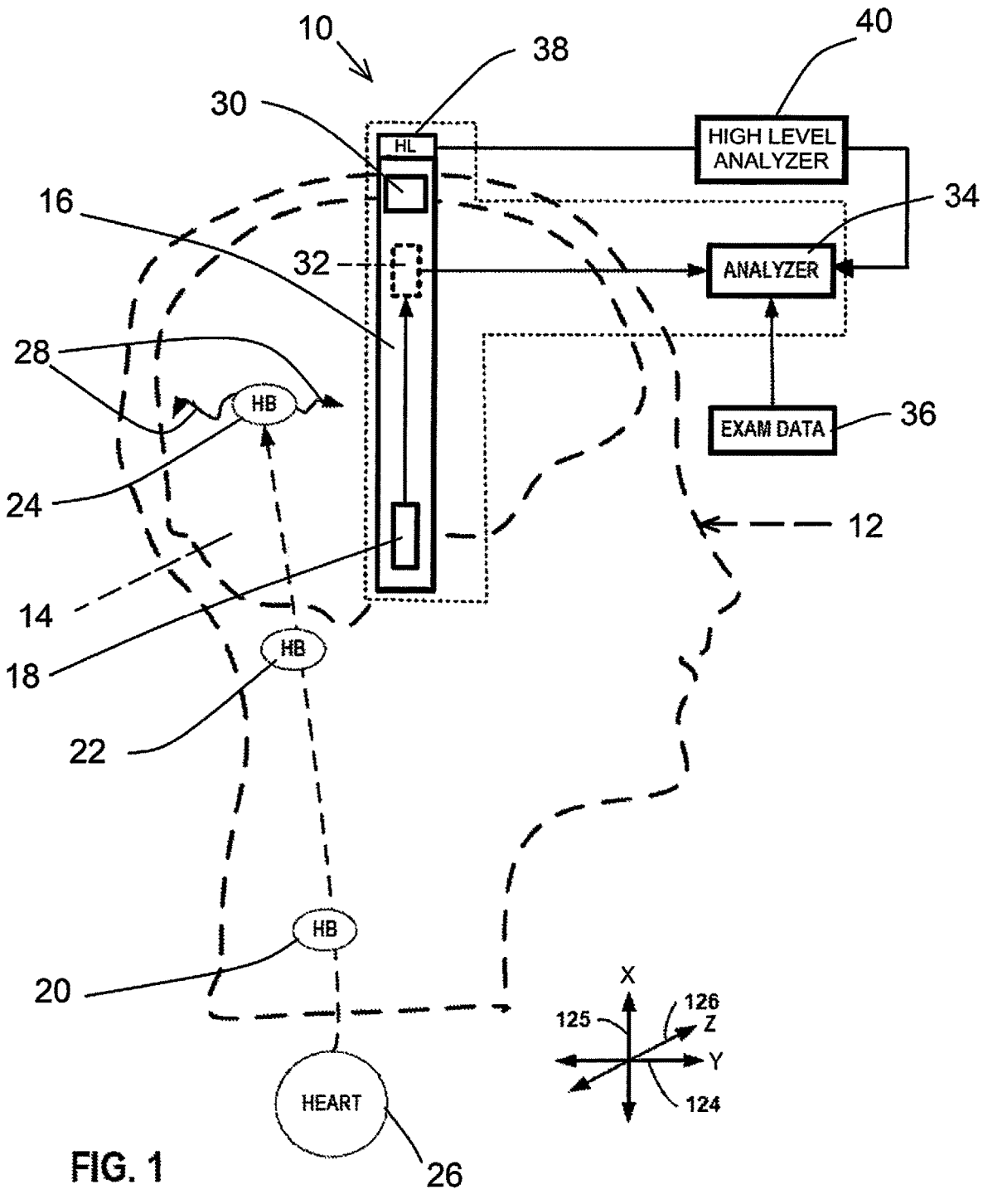
FIG. 1 is a schematic elevation view indicating the head of a subject fitted with a device of the invention, with associated analysis and monitoring equipment.

FIG. 1 schematically shows a system 10 according to the invention, indicating a subject's head in profile at 12, and with the subject's brain indicated, also in dashed lines, at 14. The system 10 includes a headset 16 worn on the head in the manner similar to a hair band. On the headset 16 is an accelerometer 18, retained securely to the headset and in a position near the subject's temple, for determining a Head-Pulse signal generated by a series of heartbeats indicated schematically at 20, 22 and 24, from contractions of the user's heart, indicated at 26. The pulsing of the heartbeat in the head causes slight physical movements of the head, i.e. of the skull, in X, Y and Z orthogonal directions, those directions being the vertical direction, anterior-posterior direction and the lateral direction. Accelerations are schematically indicated by arrows 28 in the drawing. Accelerations in one, two or all of these directions can be sensed with the accelerometer 18, with a multi-axis accelerometer preferably provided (although a single axis accelerometer can be used). An important aspect is that acceleration data can be taken at a single location on the head.

The headset is preferably wireless and thus includes a battery indicated at 30, although a non-wireless form of the headset could be provided, receiving power through a cable.

The wireless device includes a wireless data transmitter or interface 32, sending data wirelessly to an analyzer 34 which could be, for example, contained in an app of a smart phone nearby. Alternatively, the analyzer 34 can be contained in the headset, and processed data can then be sent by cable or wirelessly to a smart phone for indication of analysis and results. In another embodiment data could be stored in memory storage on the headset itself, to be retrieved at an appropriate time. The data could be stored in a removable memory such as a card, cartridge or memory stick.

The drawing also indicates that examination or clinical data 36, obtained contemporaneously through other observations or instrumentation, can be fed to the analyzer 34 for correlation with the HeadPulse signal and any transforms, typically to the frequency domain.

As part of the system 10 of the invention, a high level or gross movement accelerometer is also included on the headset device, as indicated at 38. This gross movement accelerometer has a function of sensing and recording high level movements as from vigorous exercise, typically in the range of 0.5 g to 20 g of acceleration as discussed above. This information, which is fed to a high level analyzer 40 and also communicated to the analyzer 34, correlates a subject's activity and events of that activity with the analyzed headpulse signals, for purposes discussed above, i.e. to determine whether a return to play (RTP) has caused biometric indication of concussion recurrence. The high level accelerometer 38 can be placed anywhere on the headset. As an alternative, as discussed above, the high level accelerometer 38 could be on a separate device such as on a FitBit device worn on the wrist or arm. Further, it could be combined with the sensitive accelerometer 18 provided a wide range accelerometer is used. In any event, the Head-Pulse signals and the high-level, gross acceleration signals are separate streams of data from the headset.

Figure 2:
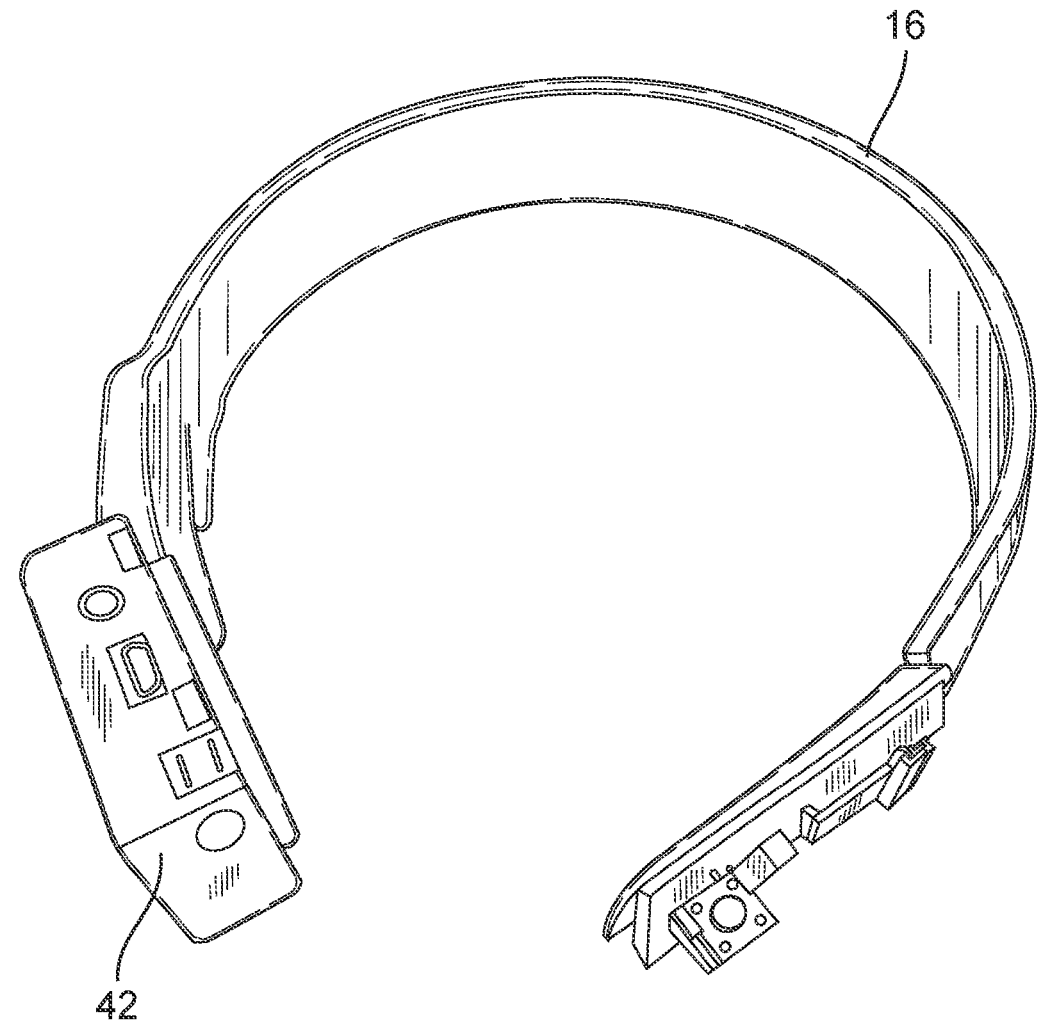
FIG. 2 is a view showing an example of a headset of the invention.

FIG. 2 shows the HeadPulse headset device 16 in a preferred embodiment. Two circuit boards are mounted on a headset similar to a plastic hairband, and interconnected by a ribbon cable extending around the band. A protective cap 42 is shown on one side, but the cap is removed at the right side for purposes of clarity. Circuit boards each contain a sensitive three-axis accelerometer in this embodiment, sampled at 250/second and stored on a micro-SD card that slides into the unit. The device has a Bluetooth interface to a custom smart phone app, indicated in FIG. 3, which also includes NSI (Neuro-behavioral System Inventory) queries. In one embodiment the subject is required to respond to all questions posed by the app with each biometric recording with HeadPulse. This system is used with the participating subjects in the study reported below. Instructions were displayed to the subject as on the leftmost panel, FIG. 3A. The NSI question responses are cell-reported using a 5 point Likert scale ranging from 0 to 4, 0 indicating "non" or no systems and 4 indicating very severe symptoms for each question. Overall symptom severity was calculated as the sum of the values provided by the subject with possible score range of 0 to 88.

The head-attachable device can take different forms. For example, it could simply be a patch (e.g. an adhesive patch) that contains both accelerometers (or at least the sensitive accelerometer) and Bluetooth or other wireless technology, along with a small battery. The data can be wirelessly sent to the cloud for processing, or the processing can occur on a smart phone or on the device itself. Note that data could be sent from the head-attached device, or from a smart phone or other device, directly to a medical professional to evaluate a patient's recovery or to provide a record of the recovery with the correlation of the high g accelerometer data and the HeadPulse, low g accelerometer data.

Concussion Study with Australian Athletes

This was a prospective cohort study. Subjects were enrolled in feasibility (A1) and validation (A2) phases. A1 was recruited between Aug. 5, 2021, and Sep. 10, 2021. A2 was recruited between May 5, 2022, and Sep. 3, 2022. The study evaluated a longitudinal cohort of concussed and control athletes of amateur Australian Rules Football (ARF) to investigate the time course of HeadPulse signal changes seen in recently concussed athletes (Australian University of California San Francisco concussion study in athletes, AUSSIE-1, A1). The model was then validated in a second cohort (AUSSIE-2, A2). Athletes in ARF do not wear padding or head protection. Concussion is a frequent complication. Recruitment occurred within the Adelaide Football League, the highest level of amateur Australian Rules Football in the state of South Australia, Australia. Adult male or female athletes participated. Controls were concussion free. All subjects provided consent at season start. HeadPulse measurements were obtained using a lab developed headset utilizing cranial accelerometry to transduce head forces (the headpulse) generated by cardiac contraction. Subjects were followed for one month with repeat recordings and completed a Neurological Symptom Inventory (NSI) with each recording.

HeadPulse waveform analysis involved frequency transformation, then evaluation using a prespecified algorithm. Calculated waveform patterns of concussed athletes were compared to control subjects using Z scores. HeadPulse concussion was characterized as Z scores>2 (2 standard deviations from control HeadPulse Z scores). Sensitivity, time of onset, and duration of HeadPulse concussion were investigated.

100 subjects participated with 58 control and 42 concussed subjects and 44 total concussions. HeadPulse biometric parameters became abnormal in 82% of injured subjects (50% identified by day 2, 90% by day 14). HeadPulse biometrics remained elevated 12 days longer than reported symptoms on average. HeadPulse abnormality exacerbations symptoms occurred in those who returned to play or engaged in unsupervised physical activity.

Results show that serial HeadPulse measurement has diagnostic value for concussion and recovery and may identify potential subconcussive changes during return-to-play within one month. This objective metric may support clinical decisions.

The study was designed to align with local procedures including concussion determination and RTP decisions. Research coordinators attended games and were alerted to players with concussion. An attempt was made to record from concussed athletes early. All but one initial recording were conducted within one hour of concussion. Coordinators traveled to subjects' homes every 1-3 days for a month following injury to obtain additional recordings. The A2 cohort was encouraged to wear a wristband accelerometer after injury to document physical activity (FitBit, Inspire 2. Alphabet, San Francisco, USA).

Recordings were obtained from a battery-powered non-invasive headset device as described above, comprised of highly sensitive accelerometers attached to a headset. The headset was placed on the subject's head in the coronal plane (FIGS. 1 and 2). The HeadPulse is comprised of forces on the head produced by cardiac contraction in the 10-15 mg (g, gravitational force unit, 9.8 m/s²) range. In A1, bilateral triaxial accelerometers were placed anterior to the ear over the temporal bone. In A2, a commercial device (Mind-Rhythm, Inc, Cupertino, CA) with a unilateral triaxial accelerometer was used.

Devices transduced the electrocardiogram (ECG) using a standard 3-lead system to provide heartrate information. Devices connected to an iPhone using Bluetooth and custom software. Recordings lasted 180 seconds in A1 and 90 seconds in A2 and were obtained in the seated position while the subject was asked to hold the head still and not to speak or chew. The A2 headset (MindSafe, MindRhythm, Inc, Cupertino, CA) was designed to provide feedback to participants when motion was detected. Subjects completed an adapted Neurobehaviorial Symptom Inventory (NSI) 23,24 on the iPhone with each recording.

Data files were submitted to custom software (MATLAB, MathWorks, Natick, MA) to analyze frequency data as previously described. Time domain accelerometry signals from the right-sided accelerometer for 45 heart beats were converted to frequency domain using Fourier transformation.

The average heartrate during recordings was derived from R-wave analysis of the ECG and provided the fundamental and harmonics of the heartrate. The frequency transform was sampled at the fundamental and successive harmonics 2-9. Concussion biometric $R_1$ was calculated as the ratio of the mean of the $5^{th}$ and $6^{th}$ harmonics to the max of harmonics 1-3 (R1), and concussion biometric, $R_2$, was calculated as the mean of the 7th and 8th harmonic divided by the max of harmonics 1-3 $R_1$ and $R_2$ values for controls were calculated.

Concussion biometric, $R_1$ and $R_2$, values were analyzed as Z scores above or below mean control values. Higher concussion biometric, $R_1$ and $R_2$, Z scores represent higher frequency shift of HeadPulse following TBI. The analysis defined any recording exceeding two standard deviations (SD) of controls to be significant, and the earliest value to exceed this threshold was defined as concussion biometric onset time of abnormality.

Concussion biometric $R_1$ and $R_2$, values and corresponding NSI scores were plotted over time. A Kaplan-Meier curve representing freedom from biometric abnormality was calculated to illustrate diagnostic sensitivity compared to controls and to illustrate latency from concussive event to first abnormal device recording. To document recovery from concussion, the duration from biometric concussion onset to a zero NSI score was tabulated; if the subject did not return to a zero NSI score during the recording period the subject was considered not clinically recovered. For subjects who did not have a threshold biometric onset time, the biometric duration was defined as zero. For subjects with threshold biometric onset, the recovery period was defined as duration from clinical concussion to time that all ratios fell under one SD from the mean. The choice of one SD was based on the observation that concussion biometric, $R_1$ and $R_2$, fell over time in a characteristic fashion, allowing for objective quantization of biometric parameters.

The study found characteristic HeadPulse changes after acute injury and marked asymptomatic HeadPulse abnormalities in those with RTP. Of 762 athlete volunteers, a total of 100 subjects had HeadPulse measurements including control (n=58) and concussed (n=43) subjects; one control subject was later concussed (so counted twice) and one concussed subject in A2 sustained two concussions separated by more than 1 month for a total of 44 concussions.

Subjects had similar years of education, female athletes had fewer self-reported prior concussions than males, and male athletes had historically played more games than female athletes (proxy for concussion exposure) but there were no significant differences of games played between control and concussion subjects within genders. Among concussed subjects, 4 (10%) had loss of consciousness (LOC), 16 (39%) had alteration in consciousness, and 7 (17%) had transient post-traumatic amnesia (PTA) at time of injury. Concussion was diagnosed by a physician in 7 (17%), team staff member in 25 (61%), the subjects themselves in 8 (20%), and 1 was unknown (2.4%). The diagnosis of concussion followed AFL guidelines. No subject sustained a concussion within the month following injury although many returned to play within this timeframe.

In A1, 40 of 184 (22%) of recordings were motion degraded. In A2, an improved device provided feedback regarding excessive body motion (MindSafe device, provided by MindRhythm, Inc, Cupertino, CA) resulting in fewer rejected recordings (24/276=8.7%).

Figure 3:
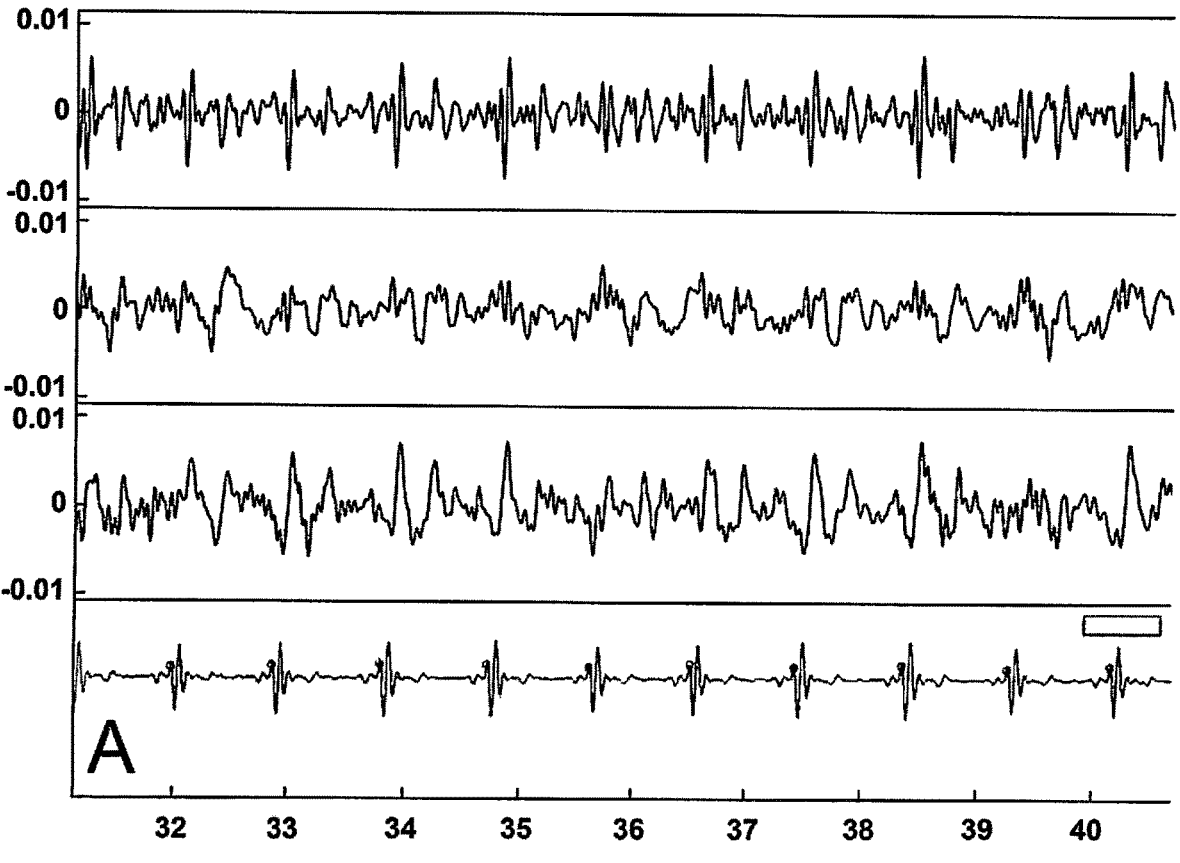
FIG. 3 is a time domain graph of the HeadPulse signal in X, Y and Z directions, representing a subject with no concussion.

FIG. 3 shows a typical HeadPulse recording, which is raw data in the time domain for each of three axes on which accelerometer readings are taken. The first three panels are HeadPulse forces, in mg (milli-g in the vertical, anterior-posterior and lateral axes, respectively (i.e. the X, Y and Z axes, respectively). The bottom trace in FIG. 3 is the ECG.

Figure 4:
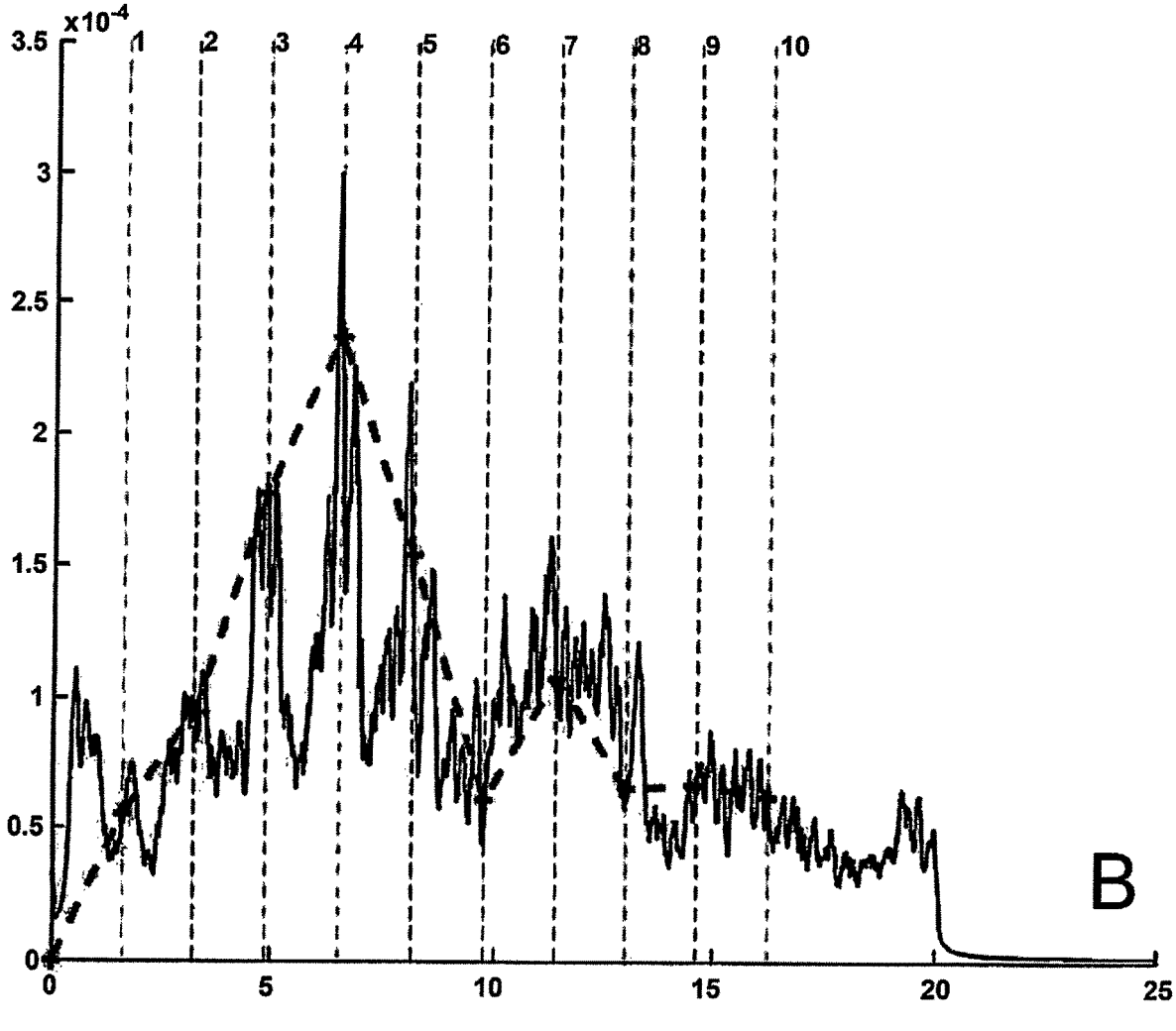
FIG. 4 is a graph showing an FFT of HeadPulse signals, showing the signals in the frequency domain. This represents a subject immediately following concussion.

FIG. 4 is the Fourier-transformed data from a time domain sample similar to that in FIG. 3, but for a subject immediately following concussion. Harmonics of the heart rate are shown as vertical dotted lines and denoted by number. The height of the frequency transform at each harmonic is used to calculate the concussion biometric, $R_1$ and $R_2$, values. Harmonics 5 and 6 are smaller than the maximum of harmonics 1 to 3 in this period immediately following concussion, i.e. within hours.

Figure 5:
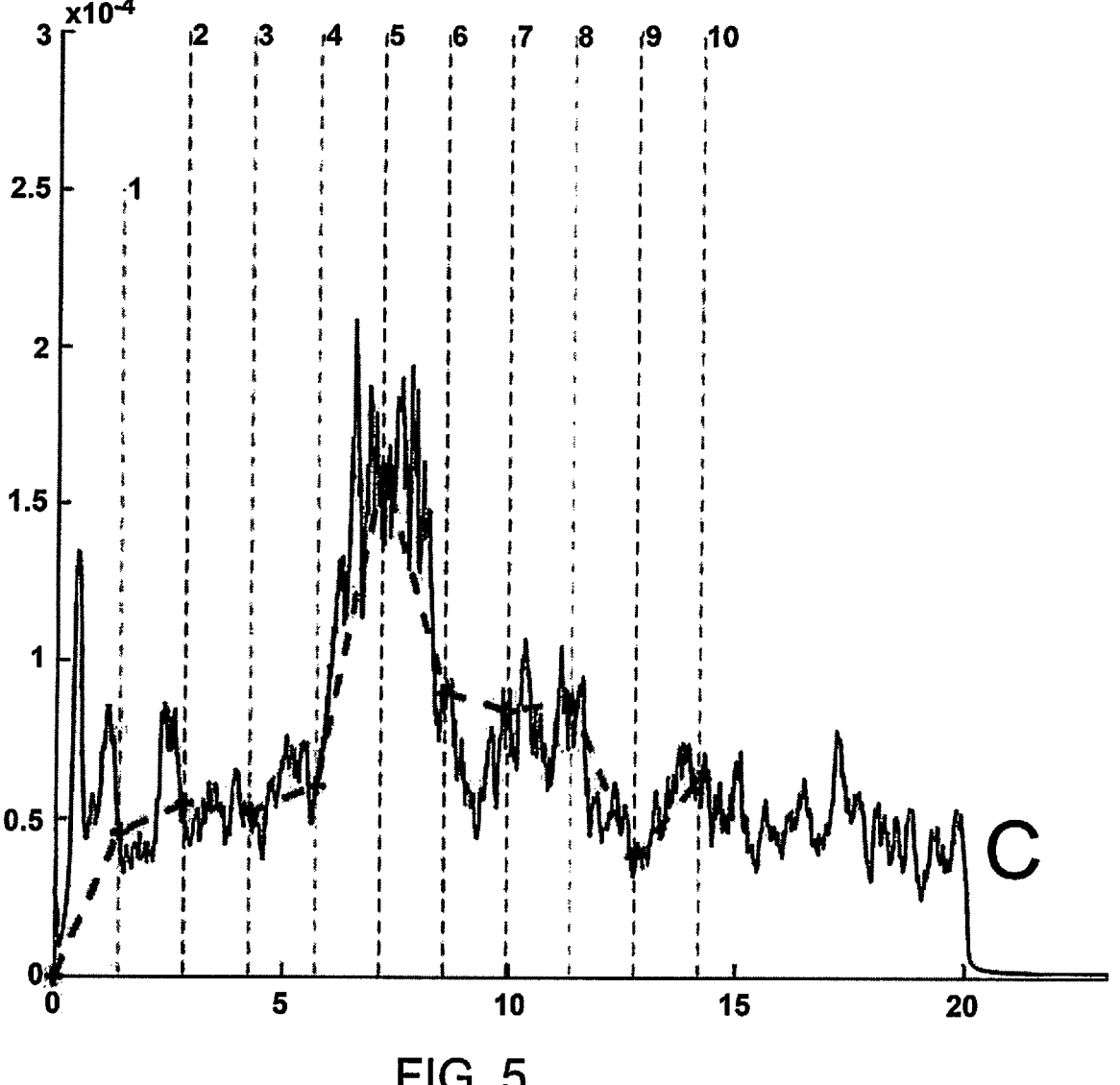
FIG. 5 is a similar frequency domain graph showing the same subject as in FIG. 4 but three days later.

In FIG. 5 the same subject is shown in the frequency domain three days later, i.e. three days after concussion. This chart shows that the fifth and sixth harmonics are now significantly greater in energy than the average of harmonics 1 to 3, defining biometric concussion. The vertical axis in these plots is frequency in Hz, i.e. energy at each frequency. Note that in FIG. 5 the rise in frequency content in the $5^{th}$ and $6^{th}$ harmonics is followed by a drop to approximately normal level at around the $9^{th}$ harmonic and then several instances of rising and falling of harmonics up to the $20^{th}$ harmonic.

Figure 6:
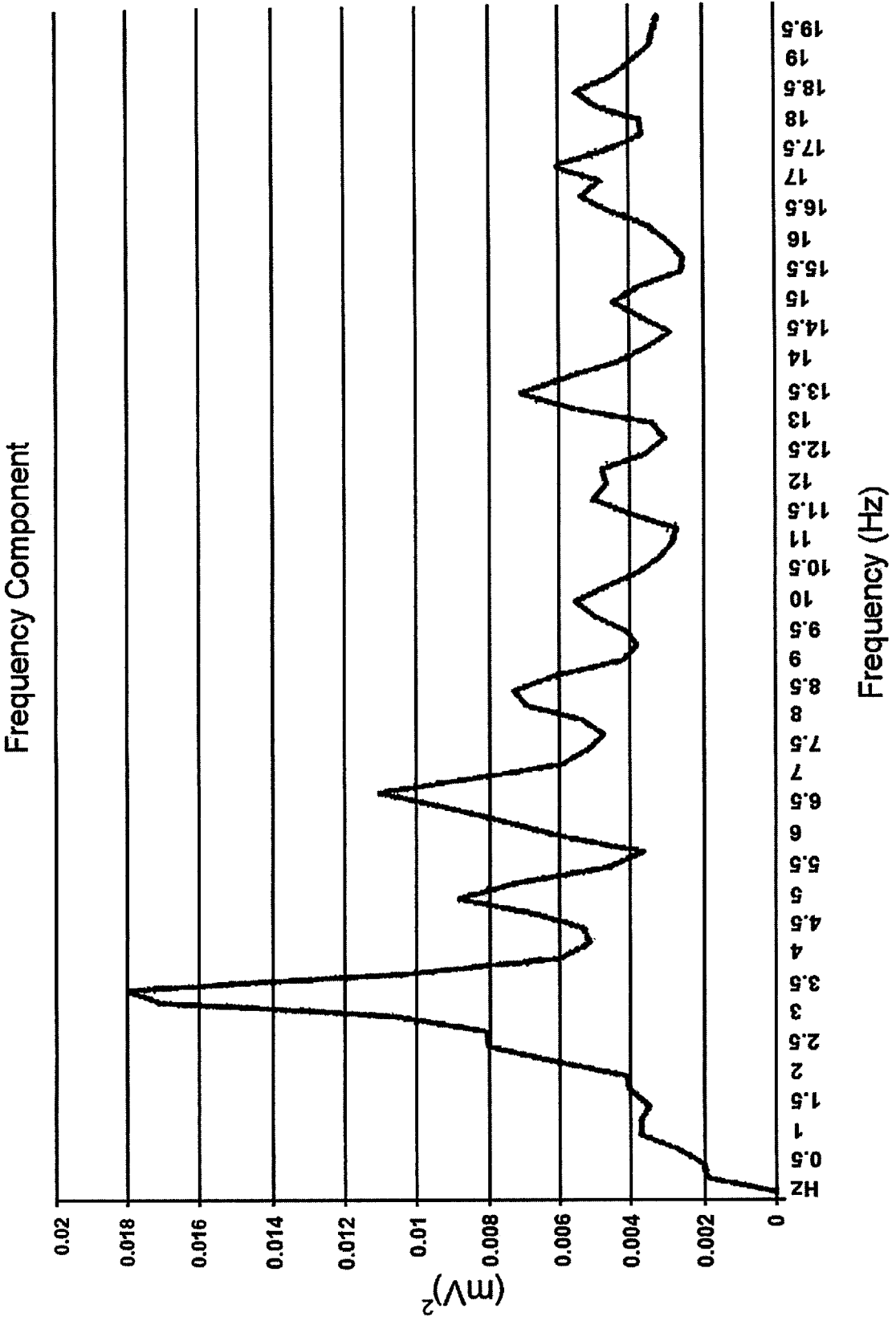
FIG. 6 is a frequency domain plot showing a subject with no concussion.

FIG. 6 is another plot of energy in the frequency domain, showing a subject with no concussion. This is very roughly similar to the graph of FIG. 4, and typical of subjects without concussion, with highest-energy frequency at about the $3^{rd}$ or $4^{th}$ harmonic.

Figure 7:
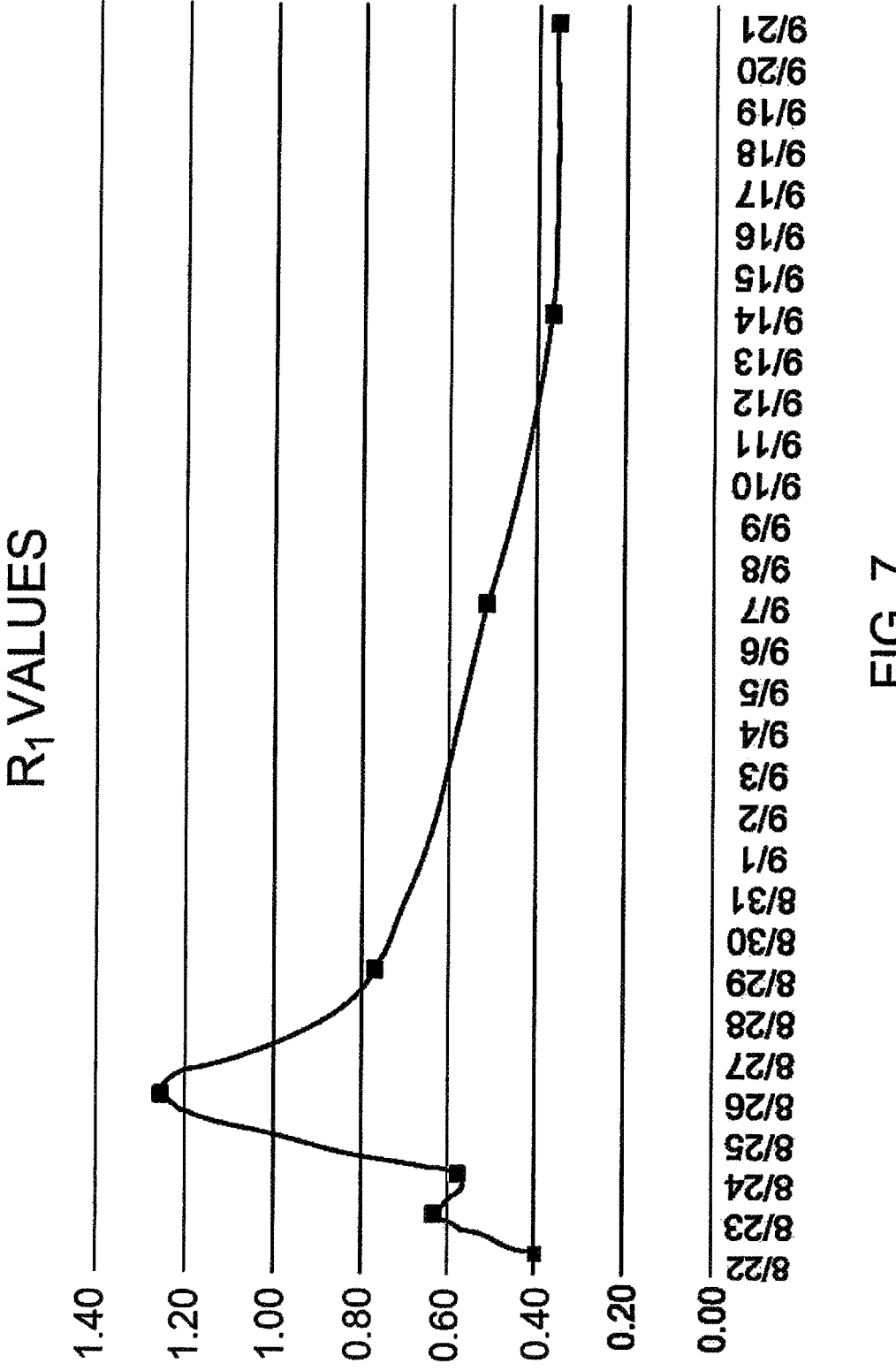
FIG. 7 is plot of a value identified as $R_1$, for a subject having concussion, with $R_1$ plotted against time in days.

FIG. 7 is a plot of concussion biometric, $R_1$ value, concussion biometric, $R_1$, being the average or mean of harmonics 5 and 6 divided by the max of harmonics 1 to 3. The plot is concussion biometric, $R_1$, value versus time in days. As is typical, the spike in concussion biometric, $R_1$, value does not occur immediately, but here began in the second or third day, reaching a peak in about the fifth day, then falling off over the next four or five days and more gradually through the third or $24^{th}$ day.

Figure 8:
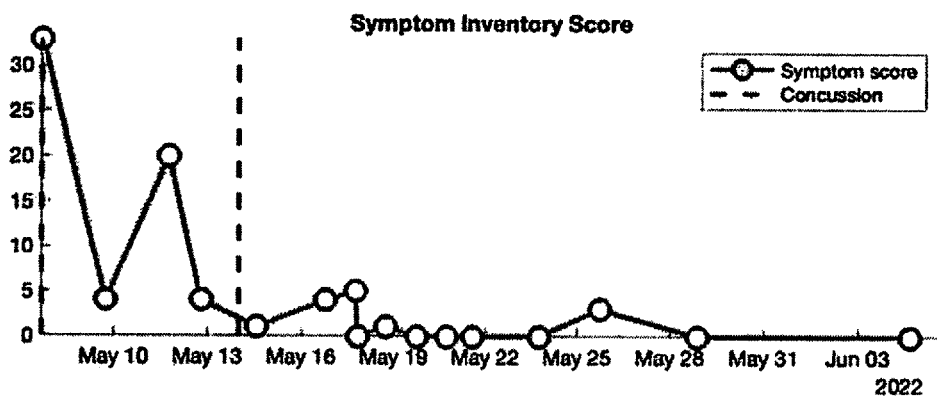
FIGS. 8 and 9 are each series of graphs comparing symptom scores or NSI of two different subjects with concussion, the NSI graph being compared with $R_1$ and $R_2$ values over a period of approximately one month, and with the subject returning to play in vigorous activity at respective numbers of days.
Figure 8:
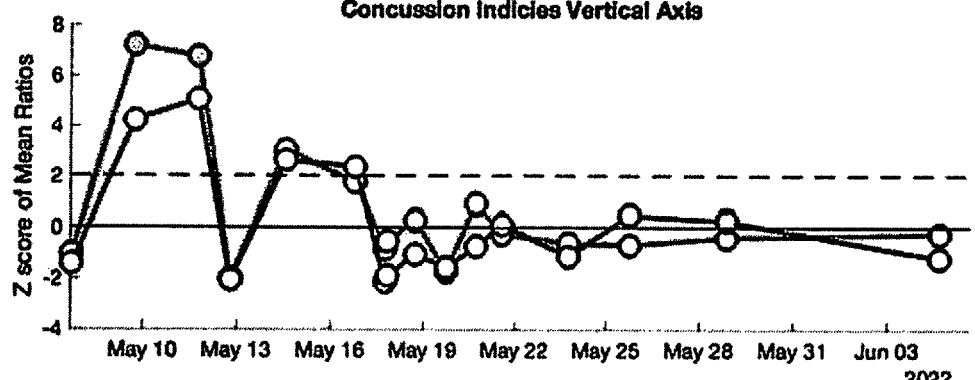
Figure 8:
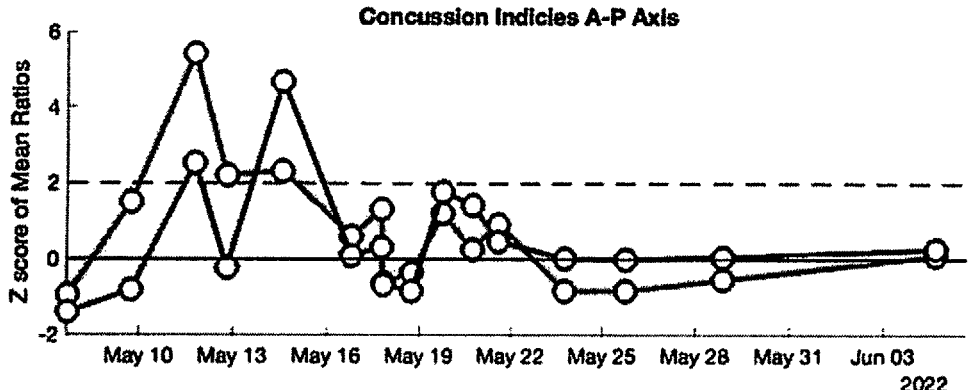
Figure 8:
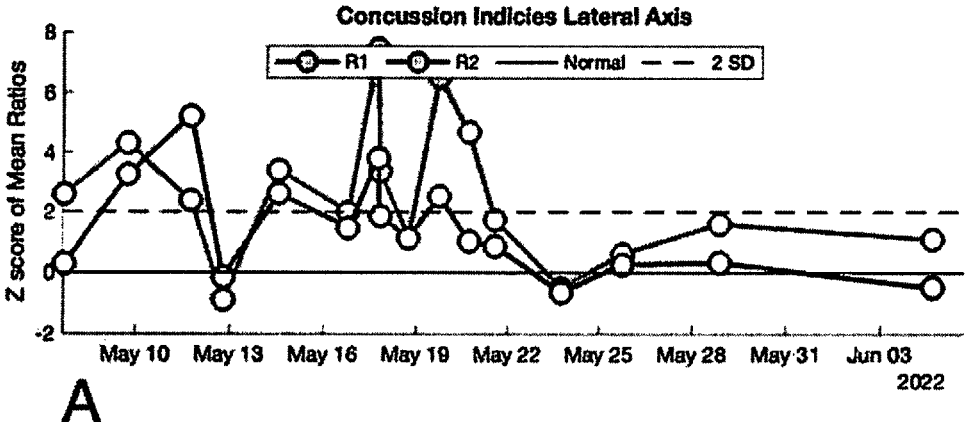
Figure 9:
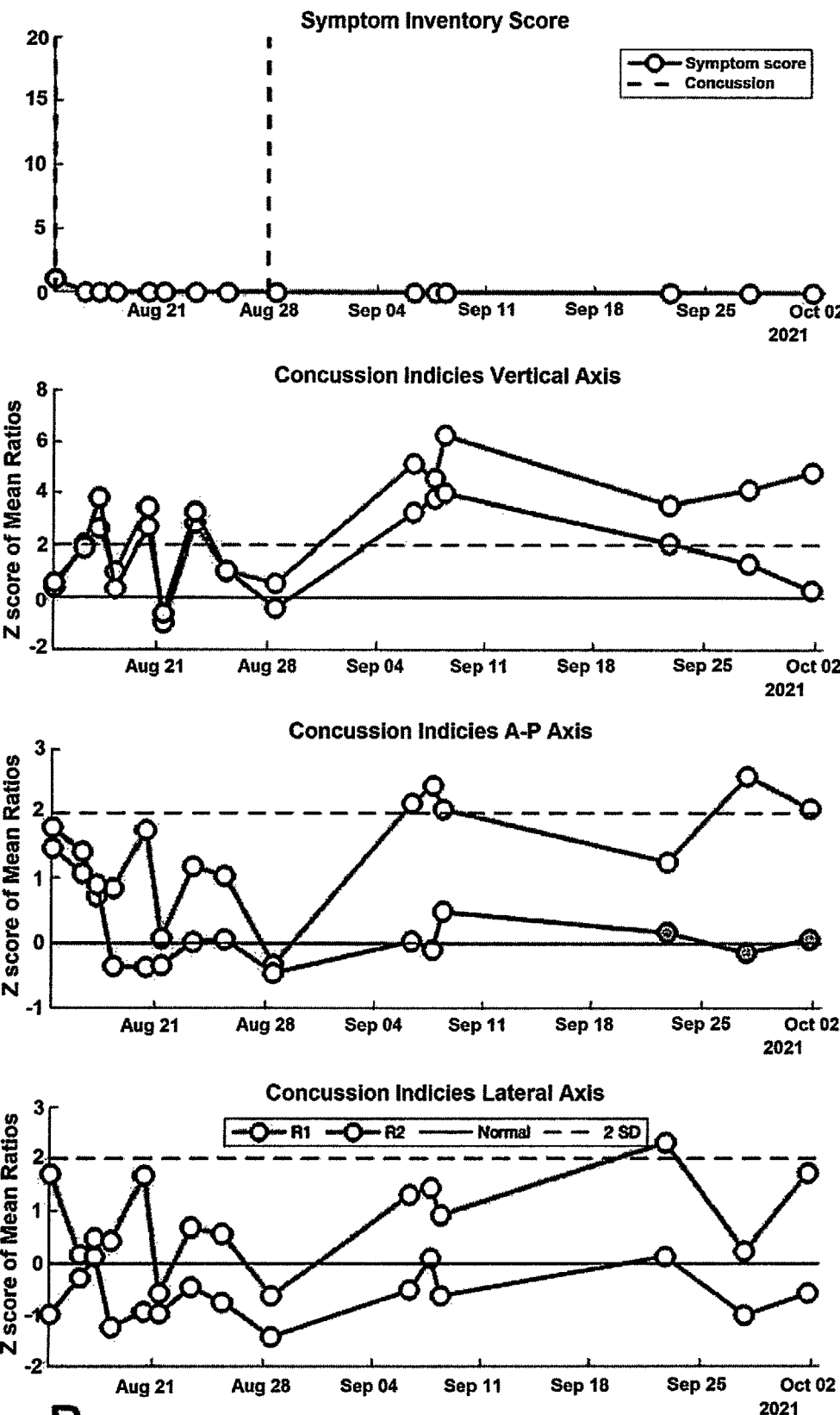

FIGS. 8 and 9 are a series of graphs that compare NSI scores against biometric data for each of two different subjects. FIG. 8 represents a female subject who sustained a concussion during an Australian Football game. The top trace is her NSI score time-locked to each HeadPulse recording over the course of a month. The dashed line at the left vertical axis is the time of concussion, and the dashed line at May 13 indicates return to play (RTP). The three graph panels below are the vertical, anterior-posterior, and lateral accelerometry HeadPulse recordings obtained while the subject was rested in the seated position. $R_1$ and $R_2$ values are shown for each recording for each of these three axes. Ordinate values are Z scores of $R_1$ and $R_2$ values compared to the mean of controls; a horizontal dashed line at level 2 indicates two standard deviations above control means. The first recording crossing the 2-SD line in any of the three axes is defined as biometric onset time of concussion, typically a day or two later than the actual time of concussion. As was typical of both cohorts (FIGS. 8 and 9) the concussion biometric, $R_1$ and $R_2$, values become abnormal on day 2, return to normal at approximately day 5 to 7, then rise and fall again in an "M-shaped" fashion. This subject was sedentary until she returned to play. As indicated in the graphs, she experienced a later rise in concussion biometric, $R_1$ and $R_2$ values on day 13, particularly on the lateral axis, then returned to normal for the remainder of the month. This is an example where the biometric signal parallels the NSI.

FIG. 9 represents a 21-year old male with two prior concussions who was knocked to the ground, stood up and was ataxic, then fell. His NSI score reveals minimal self-reported systems, and his cranial accelerometry recordings show significant rise/fall/rise/fall pattern as identified with the cohort in FIG. 8. Having no concussion symptoms according to the NSI reporting, he was returned to play on day 13, shown at August 28, and did not have a return of symptoms. Despite being asymptomatic, his biometric parameters rose above two standard deviations (approximately September 1, day 17) and did not return to normal within the period measured. This is an example where the biometric signal is independent of the NSI.

Figure 10:
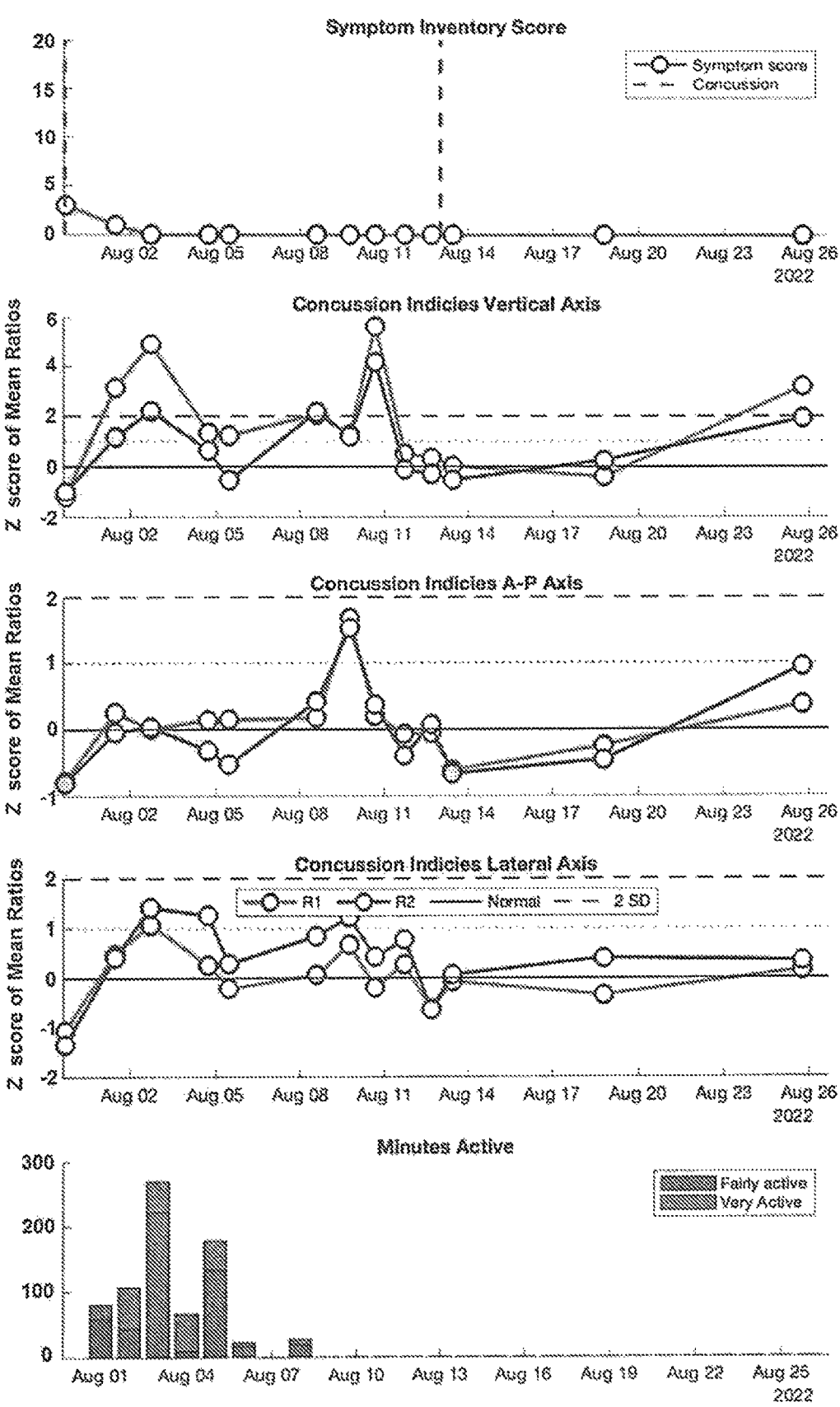
FIG. 10 is a similar series of graphs showing another subject with concussion, this one returning to play early during the period of concussion.

FIG. 10 shows a similar graph comparison of NSI versus biometric, for a 19-year old male subject with known prior concussions, sustaining a concussion during an Australian football game. The figure layout is similar to FIGS. 8 and 9, with symptom score, NSI, shown in the top trace and concussion biometric $R_1$ and $R_2$ plotted in the lower three graphs, for the same three acceleration axes as in FIGS. 8 and 9. In FIG. 10 the subject's level of activities is plotted by date in the bottom graph. In addition to the HeadPulse recordings, this subject wore a wrist-mounted accelerometer. Activity in the bottom graph is defined as "fairly active" and "very active" by the device manufacturer (FitBit, Alphabet, San Francisco). The wrist-mounted device documented significant physical activity in the days preceding the rise at day 10 before the subject returned to play on day 14 (as indicated in the NSI graph at the top). Four other subjects had good quality wrist-accelerometry and all four had worsening of the biometric following initiation of exercise. FIG. 10 shows that in the case of the 19-year old male subject, the subject was not concussion free at the end of the duration of testing, which is shown as 28 days. On both the vertical axis and the A-P axis, the subject's $R_1$ or $R_2$ value did not return to below one standard deviation during that period.

Figure 11:
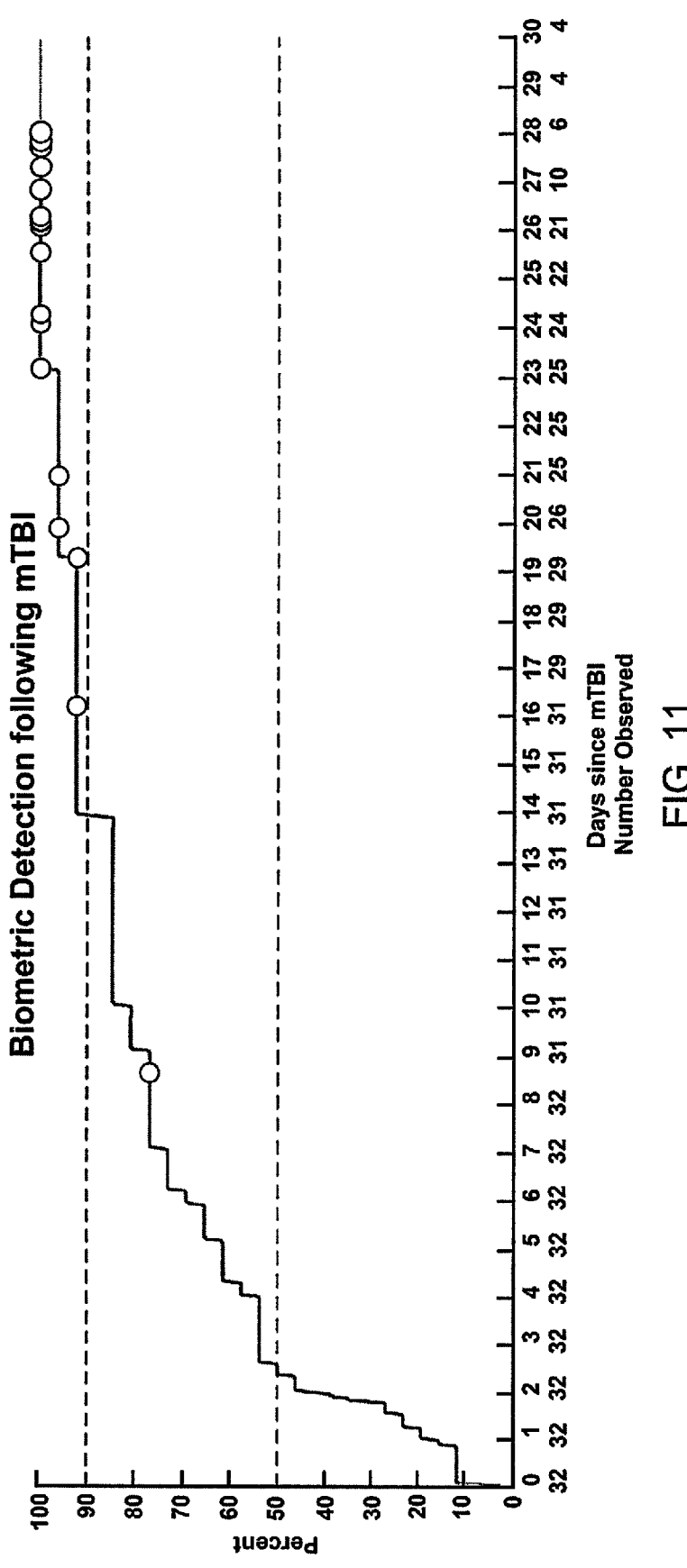
FIG. 11 is a graph representing percentage of subjects of a large group indicating biometric concussion over a month of time.

FIG. 11 is a graph that includes all subjects enrolled with concussion. This shows the proportion of participants exhibiting HeadPulse biometric parameters that exceed 2 SD (Z>2) of control subject over thirty days. This included both the A1 and A2 cohorts who had more than one recording. Overall, 26/32 (81%) of subjects with the clinical diagnosis of concussion had concussion biometric onset of concussion in the first thirty days. Of these 26 subjects, on the day of concussion (day 0) 11% were abnormal, 50% were abnormal between days 2 and 3 (lower dashed line), and 90% of concussion detected subjects were abnormal on day 14 (upper dashed line). Small circles on the chart indicate censoring of subjects. Censoring means a subject has no further observation after that time.

Figure 12:
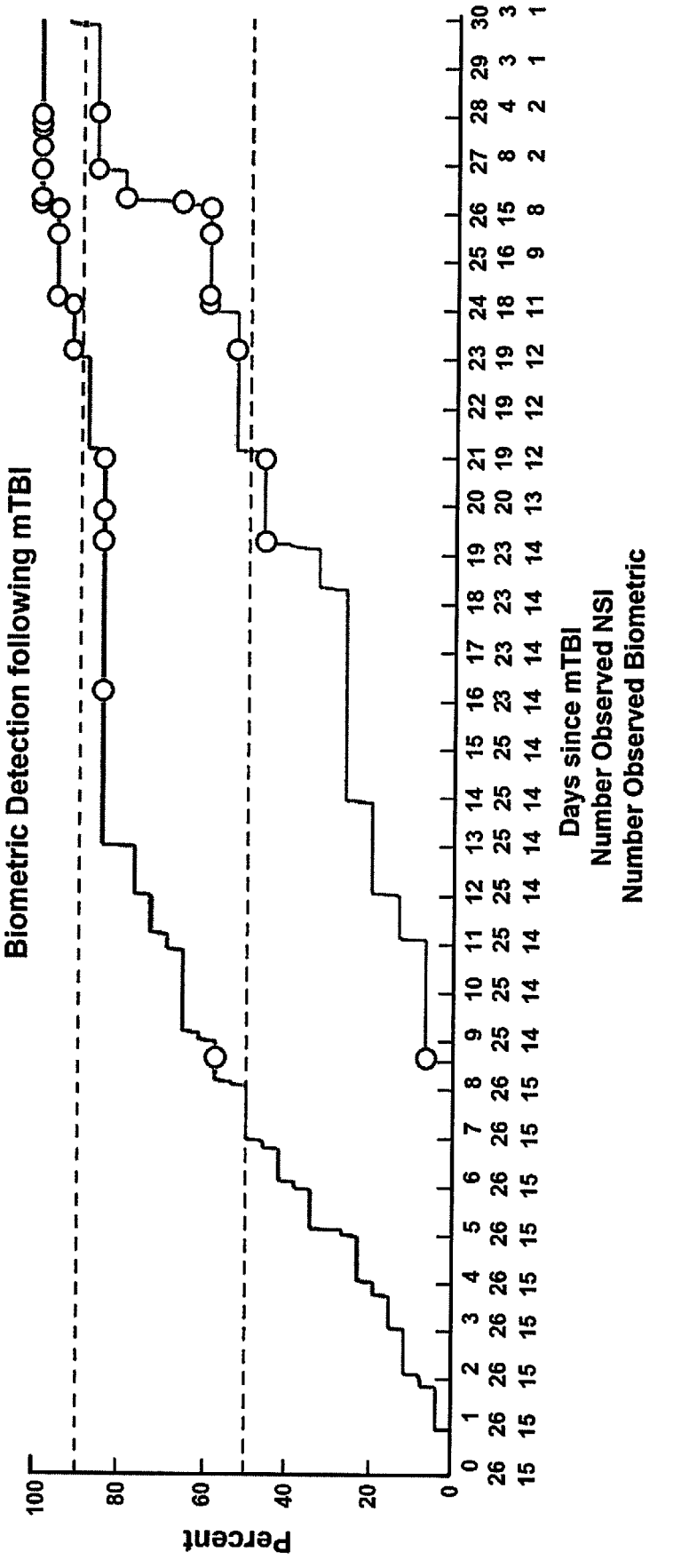
FIG. 12 is graph showing percentage of concussion subjects who appear to achieve concussion free status based on NSI values, and with a lower line showing percentage achieving biometric indication of concussion free status, over a period of one month.

FIG. 12 is another graph showing concussion versus time in days for the subjects who recovered by two criteria: recovered by NSI returning to zero score, and biometric ratios returning to within one SD of control values. The upper trace represents the NSI score returning to zero and the lower trace represents return of biometric ratios to within one SD of controls. Fifty percent of subjects had zero NSI values on day 7, while 50% of subjects had recovery of the biometric ratios by day 21, 14 days later. This suggests that biometric abnormalities resolve around 14 days following traditional definitions of concussion recovery.

The procedure and system of the invention greatly improve determination of recovery from concussion, indicating that NSI scores are not reliable to determine safe return to strenuous activity. RTP too soon is shown to aggravate concussion and increase concussion biometrics, indicating strenuous activity has been resumed too early.

The invention applies not only to sports as relates to concussion, but to all activities where jarring of the head can occur, such as military and industrial activities, vehicle accidents, physical attacks, etc.

The above described preferred embodiments are intended to illustrate the principles of the invention, but not to limit its scope. Other embodiments and variations to these preferred embodiments will be apparent to those skilled in the art and may be made without departing from the spirit and scope of the invention as defined in the following claims.

I claim:

1. A method for detecting status of recovery from brain concussion in a human patient, by detection and measuring of natural minute motions of the patient's head due to blood flow in the brain and resultant movement of tissue in the brain, comprising:

providing a head-attachable sensor device including a first accelerometer sensor, being a low-level accelerometer sensitive to said natural minute motions of the head, providing a second accelerometer sensor securable to the patient, the second accelerometer being a high-level accelerometer sensitive to larger accelerations in a range of 0.5 g to 100 g from gross movements related to jarring, impacts or sudden movements of the patient, the first and second accelerometer sensors providing two separate streams of acceleration signal data, both the sensors being connected to a computer which receives and records the two separate streams of accelerometer signal data from the first and second sensors, with the patient having a confirmed concussion, after a selected number of days following onset of concussion, attaching the head-attachable sensor device on the patient's head such that the first accelerometer sensor contacts the head so as to produce a first data stream to record frequency of the natural minute motions of the skull on at least one axis at the location of the first sensor, including a frequency range up to 25 Hz, attaching the second accelerometer sensor to the patient such that the second accelerometer sensor detects and measures and produces a second data stream to record the larger accelerations or gross movements of the patient from jarring, impacts or sudden movements, in a range of 0.5 g to 100 g, after the patient engages in physical activity wearing at least the second accelerometer sensor, receiving and recording with the computer, the separate streams of signal data from the first and second accelerometer sensors, representing said natural minute motions in the head as well as the gross motions from sudden movements, jarring or impacts, with the computer, comparing said signal data with data corresponding to non-concussion, to determine occurrence of and magnitude of any increase in frequency content of skull motion with the first accelerometer sensor, in frequency ranges above about the fourth harmonic of the patient's heartbeat, indicative of non-recovery from concussion, while verifying the patient's physical activity prior to or concurrent with the time of the data with the second accelerometer sensor as a cause of any detected increase in frequency content, and restricting the patient from said physical activity if the comparison by the computer is indicative of non-recovery from concussion.

2. The method of claim 1, further including, in the event non-recovery from concussion is indicated, continuing to monitor signal data from the first and second sensors and, when the patient again returns to physical activity, determining whether concussion is still indicated, and repeating this procedure until physical activity ceases to be indicative of non-recovery of concussion.

3. The method of claim 1, wherein the second accelerometer sensor is contained in the head-attachable sensor device.

4. An apparatus for detecting status of recovery from brain concussion in a human patient, by detection and measuring of natural HeadPulse motions of the patient's head due to blood flow in the brain and resultant movement of tissue in the brain, comprising:

a head-attachable device including a first accelerometer sensor, being a low-level accelerometer sensitive to said natural HeadPulse motions of the head, a second accelerometer sensor device attachable to the patient and being a high-level accelerometer sensitive only to larger gross movements relating to jarring or impacts during physical activity, the head-attachable device with the first accelerometer sensor, and the second accelerometer sensor device, including electronics connected to the sensors for receiving respective first and second acceleration signals and generating respective first and second separate streams of digital acceleration signal data, and an analyzer connected to the electronics, for determining any elevation in frequency content of the HeadPulse motions with the first accelerometer sensor, in frequency ranges above about the fourth harmonic of the patient's heartbeat, indicative of non-recovery from concussion, and for correlating any such increase in frequency content with any larger, gross movements due to jarring or impacts to the patient as confirmed by the second stream of accelerometer data from the second accelerometer sensor device, whereby if non-recovery is indicated in the patient at a time weeks after confirmation of concussion, the patient's physical activity prior to the time of the signal data from the first acceleration sensor can be verified with the second accelerometer sensor device as a cause of the detected increase in frequency content, and whereby if recovery is indicated in the patient at said time and the patient then engages in physical activity after which first acceleration data again shows increase in frequency content of HeadPulse above about the fourth harmonic of heartbeat, recovery from concussion is contra-indicated and the patient can be advised to refrain from such physical activity.

5. The apparatus of claim 4, wherein the second acceler-ometer sensor device is included in the head-attachable device so as to detect the jarring movements of the head.

6. The apparatus of claim 5, wherein the analyzer is located remotely from the head-attachable device, connected thereto wirelessly.

7. The apparatus of claim 5, wherein the analyzer is incorporated in the head-attachable device.

8. The apparatus of claim 7, wherein the head-attachable device comprises a wearable headset.

9. The apparatus of claim 5, in combination with a smart phone, the apparatus and the smart phone having wireless communication capability so that the smart phone displays and reports any said increase in frequency content.

10. The apparatus of claim 4, wherein the analyzer is located remotely from the head-attachable device, connected thereto wirelessly.

11. The apparatus of claim 4, wherein the head-attachable device comprises a wearable headset.

* * * * *